US00PP26624P2

(12) United States Plant Patent
Hansen

(10) Patent No.: US PP26,624 P2
(45) Date of Patent: Apr. 19, 2016

(54) ***BAPTISIA* PLANT NAMED 'BROWNIE POINTS'**

(50) Latin Name: ***Baptisia* hybrid**
Varietal Denomination: Brownie Points

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 169 days.

(21) Appl. No.: 14/120,590

(22) Filed: Jun. 6, 2014

(51) Int. Cl.
*A01H 5/02* (2006.01)

(52) U.S. Cl.
USPC ..... Plt./263.1

(58) Field of Classification Search
USPC ..... Plt./263.1
CPC ..... A01H 5/02
See application file for complete search history.

*Primary Examiner* — Kent L Bell

(57) ABSTRACT

A new and distinct plant cultivar of hardy herbaceous False Indigo named *Baptisia* 'Brownie Points' characterized by compact vase-shape habit in lower portion with upright spreading stems forming a mound in the upper portion with upright stems and several large, chocolate-brown colored flowers on well-branched stems held well mostly above light green to chartreuse foliage in the late spring, suitable for landscaping as a specimen or en masse.

1 Drawing Sheet

Botanical classification: *Baptisia* hybrid.
Cultivar designation: 'Brownie Points'.

BACKGROUND OF THE INVENTION

The present invention relates to a new and distinct cultivar of hybrid *Baptisia* plant, botanically known as *Baptisia* 'Brownie Points' and will be referred to hereafter by its cultivar name, 'Brownie Points'. The new cultivar represents a new false indigo, a hardy herbaceous perennial grown for landscape and cut flower use.

The new invention arose from a long term breeding program at a nursery in Waseca, Minn. and continued at a wholesale perennial nursery in Zeeland, Mich. with the specific intention of improving garden worthiness of perennial False Indigo plants with a wider variety of flower colors and improved garden habit.

*Baptisia* 'Brownie Points' was a selection of a specific unreleased but unidentified proprietary hybrid of *Baptisia sphaerocarpa* and the male or pollen parent was an unknown *Baptisia* from an open pollinated isolation block selection consisting of proprietary complex hybrids. Also in the isolation block were advanced hybrids of *Baptisia minor, australis, alba*, and *cinerea*.

Seeds were collected from individual selected female plants in fall of 2009 at the isolation block in Waseca, Minn., USA by the inventor. The exact identity of the female and male parent is not known but both were from proprietary unreleased and non-patented plants. Either or both parents had a high percentage of *Baptisia sphaerocarpa*. The seeds were sown by the inventor in Zeeland, Mich., USA in the fall of 2009 with the initial selection made in the spring of 2012 and the new plant was assigned the breeder code "intense brown." Asexual propagation by cuttings was initially propagated in spring 2012 at a wholesale perennial nursery in Zeeland, Mich. The results of asexual propagation are that the new plant is stable and retains its true characteristics though successive generations of asexual propagation. Propagation method for asexually reproducing plants is primarily stem cuttings. Sterile plant tissue culture can also be used for asexual propagation.

The nearest comparison plant is *Baptisia* 'Cherries Jubilee' U.S. Plant Pat. No. 23,907 which differs from the new plant in having maroon tinted yellow flowers. *Baptisia sphaerocarpa* 'Screamin' Yellow' (not patented) produces yellow flowers on upright stems, but with no brown tinting. Rare plants of *Baptisia tinctoria* may develop slight brown or dark purple tinting to the mainly yellow flowers, but the leaves are much smaller, the flowers are smaller and not on tall upright stems. These are the nearest comparison plants known to the inventor and *Baptisia* 'Brownie Points' is distinct from these and all other *Baptisia* plants known to the inventor.

The new plant differs from all *Baptisia* known to the inventor in the following combined traits:

1. Compact vase shape habit in lower portion with upright spreading stems forming a mound in the upper portion.
2. Several chocolate-brown colored flowers on well-branched stems held mostly above the foliage in spring.
3. Young foliage and stems with light green to chartreuse coloring.

BRIEF DESCRIPTION OF THE DRAWINGS

The photographs of the new plant demonstrate the unique traits of the new plant and the overall appearance. The colors are as accurate as reasonably possible with color reproductions. Variation in ambient light spectrum, source and direction may cause the appearance of minor variation in color. The accompanying photograph is of a three-year old plant growing in an open full-sun trial garden in Zeeland, Mich.

DETAILED BOTANICAL DESCRIPTION OF THE PLANT

Figure 1:
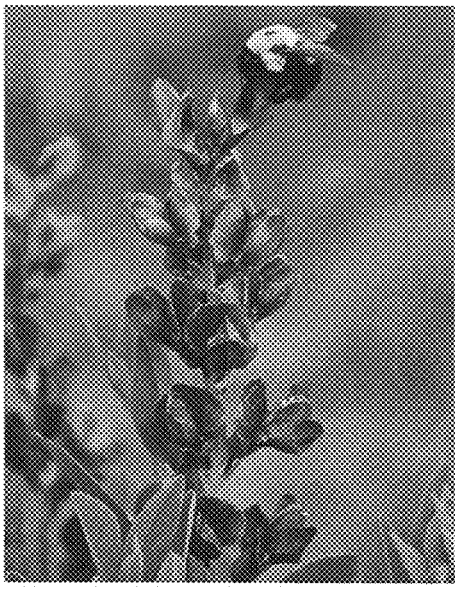
FIG. 1 shows a close-up of the flower scape.
Figure 2:
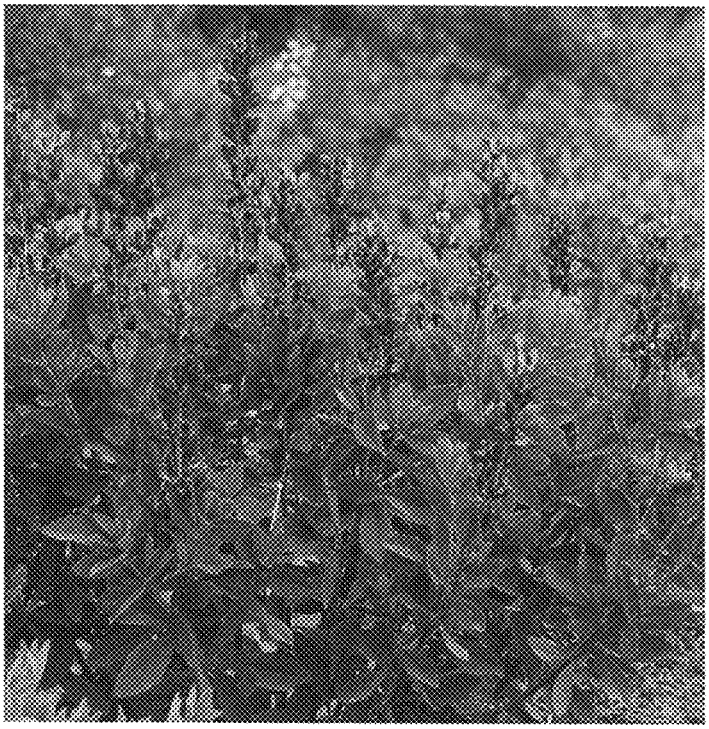
FIG. 2 shows the habit of a plant in full flower.

The following is a detailed description of 3 year-old plants of *Baptisia* 'Brownie Points' as grown outdoors in a trial plot at a wholesale nursery in Zeeland, Mich. Plants of the new cultivar have not been tested under all possible conditions. The phenotype may vary with changes in environment, climate, and cultural conditions without change however in the genotype. The color reference is in accordance with The 2001 edition of The Royal Horticultural Society Colour Chart except where general color dictionary terms are used.

Plant habit: Perennial, compact, well-branched, many-stemmed, vase-shaped growth habit with long inflorescences held above the foliage.

Plant size: About 85 cm tall from soil to top of flowers and 85 cm wide just below initial flowers.

Roots: Fibrous, well-branched, long, deeply rooted.

*Root color*.—Nearest RHS 159D.

Growth and propagation:

*Propagation method*.—Stem cuttings, rooting in about three weeks; also can be propagated successfully by sterile plant tissue culture.

*Growth rate*.—Moderately, similar to other *Baptisia*.

Stems: Rigid and upright; glaucous; glabrous; cylindrical with faint longitudinal furrows; lower two to three nodes without leaves or branches; normally 40 to 45 stems per plant; main stem about 9.0 mm diameter at base and 85.0 cm tall to top of inflorescence, average about 74.0 cm tall and 8.0 mm diameter; normally about four to five alternately-arranged primary branches beginning at the second or third node above soil and extending from stem at 45 to 60 degree angle above horizontal, up to 44.0 cm long and 4.0 mm diameter, average for primary branches about 38.0 cm long and 4.0 mm diameter, smaller distally; and three alternately-arranged secondary branches per stem of about 32 cm long and 3.0 mm diameter, averaging about 16.0 cm long and 3.4 mm diameter; normally four alternately-arranged tertiary branches up to 10.0 cm long and 3.0 mm diameter, average about 8.5 cm long and 3.0 mm diameter.

*Stem color*.—Base nearest RHS N144B without glaucous bloom and more green than RHS 122D with glaucous bloom.

*Stem scales*.—At stem nodes; slightly glaucous; dehiscing to leave behind thin scar; about 3.3 cm long and taper toward base of 24 mm across; frequently with apical three sharply pointed lobes about 1.0 mm long and 0.5 mm wide in center of retuse apex with acute tips or with three leaflets 9.0 mm long and 2.4 mm across in the center of the retuse apex; truncate base.

*Stem scale color*.—Between RHS 138C and RHS 138D before dehiscing and between RHS N199B and RHS N199C after dehiscing.

*Internodes*.—Up to 12.5 cm apart between lowest branches, average about 8.5 cm; color of scar remaining nearest RHS 11D.

Foliage: Alternate on stem; ternate to palmately compound with three leaflets; outer two leaflets at about 60 to 80 degree angle to middle leaflet; leaves up to 5.5 cm long and 10.0 cm wide, leaflet average 3.2 cm long and 4.0 cm wide.

*Leaflet*.—Three, oblanceolate; apex obtuse to rounded, base attenuate; margins entire; petiolate; top surface matte, scaberulose below; size up to 4.0 cm long and 2.0 cm wide, average about 3.5 cm long and 1.5 cm wide.

*Leaflet color*.—Newly expanding nearest RHS 144A on upper and lower surfaces; mature upper and lower surface between RHS 138B and RHS 138C.

*Venation*.—Pinnate, glabrous, thin, not conspicuous.

*Vein color*.—Newly expanding foliage midrib nearest RHS 146C above and nearest RHS 146D below; mature foliage midrib between RHS 144D and RHS N144D above and nearest RHS 139D below; secondary veins same color as surrounding leaf tissue.

*Petioles*.—Glabrous; slightly glaucous; concaved facing upward; up to about 5.0 cm long and 2.5 mm wide average 2.0 cm long and 2.0 mm wide.

*Petiole color*.—Nearest 138B on upper and lower surfaces.

*Stipules*.—Glabrous, glaucous, lanceolate, acute apex with base truncate to stem; up to 3.5 cm long and 6.0 mm wide, average 1.2 cm long and 3.0 mm wide with largest stipules below primary branches and decreasing in size distally and on secondary branches.

*Stipule color*.—Between RHS 138A and RHS 137B both surfaces with basal one quarter lightening to RHS N144D.

Flower: Zygomorphic, papilionaceous, non-secund, held at about 50 degree angle above horizontal; beginning about 45 cm above soil; up to about 30 flowers per main raceme and about 28 per secondary branch; seasonally effective for about two to three weeks beginning in late May in Zeeland, Mich. with about 36 flowers and 16 buds showing color during peak per stem; individual flower remain effective and on raceme for about four days; individually about 2.3 cm long, 1.8 cm tall and 7.5 cm wide at tallest and widest portions; comprising an upper banner, a lower keel made up of two lobes folded around gynoecium and androecium; and two lateral wings or alae laterally appressed against keel.

*Flower fragrance*.—None detected.

*Peduncle*.—Rounded with slight vertical furrows; glaucous; glabrous; from first flower to apex about 30 cm long; diameter at the base of first flower about 3.0 mm and about 2 mm diameter at the apex.

*Peduncle color*.—Nearest RHS 144A.

*Pedicel*.—Round in cross section, glabrous, slightly glaucous; about 8.0 mm long and 1.0 mm diameter.

*Pedicel color*.—Nearest RHS 144A.

*Calyx*.—Campanulate, four-lobed with top lobe pressed along banner and other lobes flared in distal region; lobes dissected about 3.0 mm deep; apex acute, base fused in basal two thirds; margins entire; slightly glaucous; about 7.0 mm long and 6.0 mm diameter; persists after petal drop.

*Calyx color*.—Abaxial nearest RHS 138B; adaxial nearest RHS 144A.

*Buds one day prior to anthesis*.—Oblong elliptic, flatted vertically; about 1.8 cm long and 8.0 mm tall and 6.0 mm wide.

*Bud color*.—Three to four days prior to opening exposed banner petal between RHS 166A and RHS N199C with distal spot nearest RHS 200C, exposed keel petal nearest RHS 11B and exposed alae petals between RHS 166A and RHS 200C; one day prior to opening exposed banner petal nearest RHS 166A with distal spot nearest RHS 200C, exposed keel petal nearest RHS 11B and exposed alae petals between RHS 166A and RHS 200C.

*Petals*.—Five; with a lower fused keel, an upper banner, and two lateral wings or alae; keel comprised of two sections that are folded around stamens and pistil. Banner petal: conduplicate, curved upward and backward and pinched in the middle; apex retuse, base claw-like, margin entire; about 1.7 cm long, 1.5 cm across at widest and 6.5 mm tall; banner dorsal side color lighter than RHS 166A but not as orange as RHS 166B with veins of nearest RHS 166A, the inner center portion nearest RHS 9C the center midrib nearest RHS 160A with very small speckles of nearest RHS 166A, claw nearest RHS 1C; banner proximal side lighter than RHS 166A but not as orange as RHS 166B with veins of nearest RHS 166A, midrib and claw nearest RHS 154A and yellow spots at base of blade nearest RHS 13C. Keel: comprised of two main lobes that are folded around stamens and pistil; fused in the distal one-third with the apex emarginate or retuse and the bases separate and claw-like; margin entire; top edge about one-third of the way from base has 2.0 mm smaller lobe pointing toward base; about 19 mm long 0.5 cm across and 7.0 mm tall with claw base narrowed to 1.0 mm wide for the proximal 5.0 mm; color of outer keel sides between RHS 1C and RHS 1D with apex nearest RHS 3C, lobe nearest RHS 11D, main vein between RHS 145B and RHS 145C, inner color same as outer color. Alae: papilionaceous corolla appendage with rounded apex and claw-like base; with 2.0 mm lobe pointing toward base and about one-third of the way from base; about 20.0 mm long and 7.5 mm tall with the claw narrowed to 2.0 mm across for the distal 5.0 mm; alae outside blade color nearest RHS 166A with veining of nearest RHS 177A; color of lobe nearest RHS 11B on inside and outside of older and younger flowers, claw color nearest RHS 1D on inside and outside; inside blade color between RHS 174A and RHS 174B.

Receptacle: Disk-shaped, about 3.3 mm diameter and 1.5 mm depth; color nearest RHS 138A.

Gynoecium: One, with superior ovary.

*Pistil*.—About 22.0 mm long and 1.5 mm wide.

*Style*.—Curved at tip, about 9.0 mm long and less than 1.0 mm diameter; color nearest RHS 145C.

*Stigma*.—Less than 0.5 mm diameter; color nearest RHS 145D.

*Ovary*.—Superior suspended by stipe; about 6 mm long and about 1.5 mm in diameter; color darker than RHS 144A.

*Stipe*.—About 4.0 mm long and 1.0 mm diameter; color nearest RHS 144B.

Androecium:

*Stamens*.—Ten, not united, about 19.0 mm long and 1.0 mm diameter.

*Filament*.—18.0 mm in length and less than 1 mm in diameter; slightly curved upward at tip; filament color nearest RHS 145D.

*Anther*.—Dorsifixed, oblong; about 1.8 mm long and 1.0 mm wide; color nearest RHS 15A.

*Pollen*.—Spherical; abundant; color nearest RHS 15A.

Fruit and seed: Have not yet been observed.

Hardiness: To USDA zones 4 to 8; heavy clay or light loamy sand soils; able to withstand drought conditions once established.

Diseases: Susceptibility or resistance to diseases beyond that typically found in other False Indigo plants has not been observed.

I claim:

1. A new and distinct cultivar of hardy herbaceous False Indigo plant named *Baptisia* 'Brownie Points' as herein described and illustrated.

* * * * *